United States Patent [19]
Binderup et al.

[11] 3,956,279
[45] May 11, 1976

[54] CRYSTALLINE PIVALOYLOXYMETHYL D(-)-α-AMINOBENZYLPENICILLINATE

[75] Inventors: Ernst Torndal Binderup, Tastrup; Hans Jørgen Petersen, Herlev; Sven Liisberg, Vedbaek, all of Denmark

[73] Assignee: Leo Pharmaceutical Products Ltd., Ballerup, Denmark

[22] Filed: Sept. 21, 1973

[21] Appl. No.: 399,736

[52] U.S. Cl. .............................. 260/239.1; 424/271
[51] Int. Cl.² ....................................... C07D 501/20
[58] Field of Search ................................. 260/239.1

[56] References Cited
UNITED STATES PATENTS 3,674,776   7/1972   Long et al. ..................... 260/243 C
3,697,507   10/1972   Freperiksen et al. ............. 260/239.1

*Primary Examiner*—Nicholas S. Rizzo
*Attorney, Agent, or Firm*—Jackson, Jackson & Chovanes

[57] ABSTRACT

The present invention relates to pivaloyloxymethyl D-(-)-α-aminobenzylpenicillinate of the formula I in a novel and improved form, i.e. the crystalline form

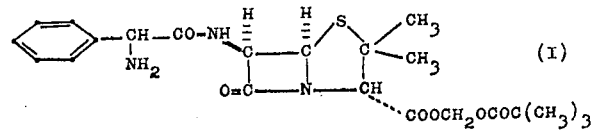

to methods of producing said crystalline pivaloyloxymethyl D(-)-α-aminobenzylpenicillinate and to pharmaceutical preparations containing said crystalline pivaloyloxymethyl D(-)-α-aminobenzylpenicillinate.

Crystalline pivaloyloxymethyl D(-)-α-aminobenzylpenicillinate has no bitter taste, is only slightly soluble in water, and is stable and readily absorbable.

1 Claim, 2 Drawing Figures

CRYSTALLINE PIVALOYLOXYMETHYL D(-)-α-AMINOBENZYLPENICILLINATE

The present invention relates to pivaloyloxymethyl D(-)-α-aminobenzylpenicillinate of the formula I in a novel form, i.e. the crystalline form

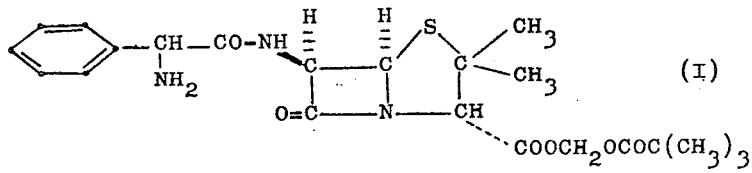

(I)

to methods of producing said crystalline pivaloyloxymethyl D(-)-α-aminobenzylpenicillinate and to pharmaceutical preparations containing said crystalline pivaloyloxymethyl D(-)-α-aminobenzylpenicillinate.

Pivaloyloxymethyl D(-)-α-aminobenzylpenicillinate in its free form is a base with the generic rINN name pivampicillin. However, due to a misunderstanding frequently seen in the literature, the term pivampicillin has often been used for e.g. the hydrochloride of pivaloyloxymethyl D(-)-α-aminobenzylpenicillinate. It shall expressly be understood that in the present specification the term pivampicillin is used with its correct rINN meaning above.

Pivampicillin, its preparation and use is disclosed in our British Pat. No. 1,215,812. Pivampicillin in the crystalline form, however, has never been described, and hitherto any attempt to obtain it in the crystalline form has been abortive, whereas some of its salts with acids are readily crystallizable.

It has now been found that it is possible to obtain the free pivampicillin in a crystalline form.

Figure 1:
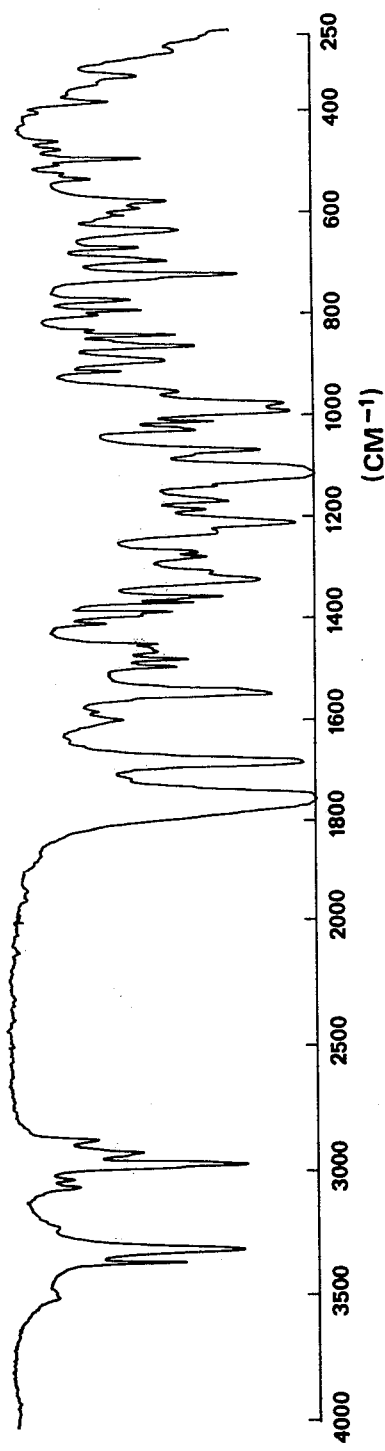
Figure 2:
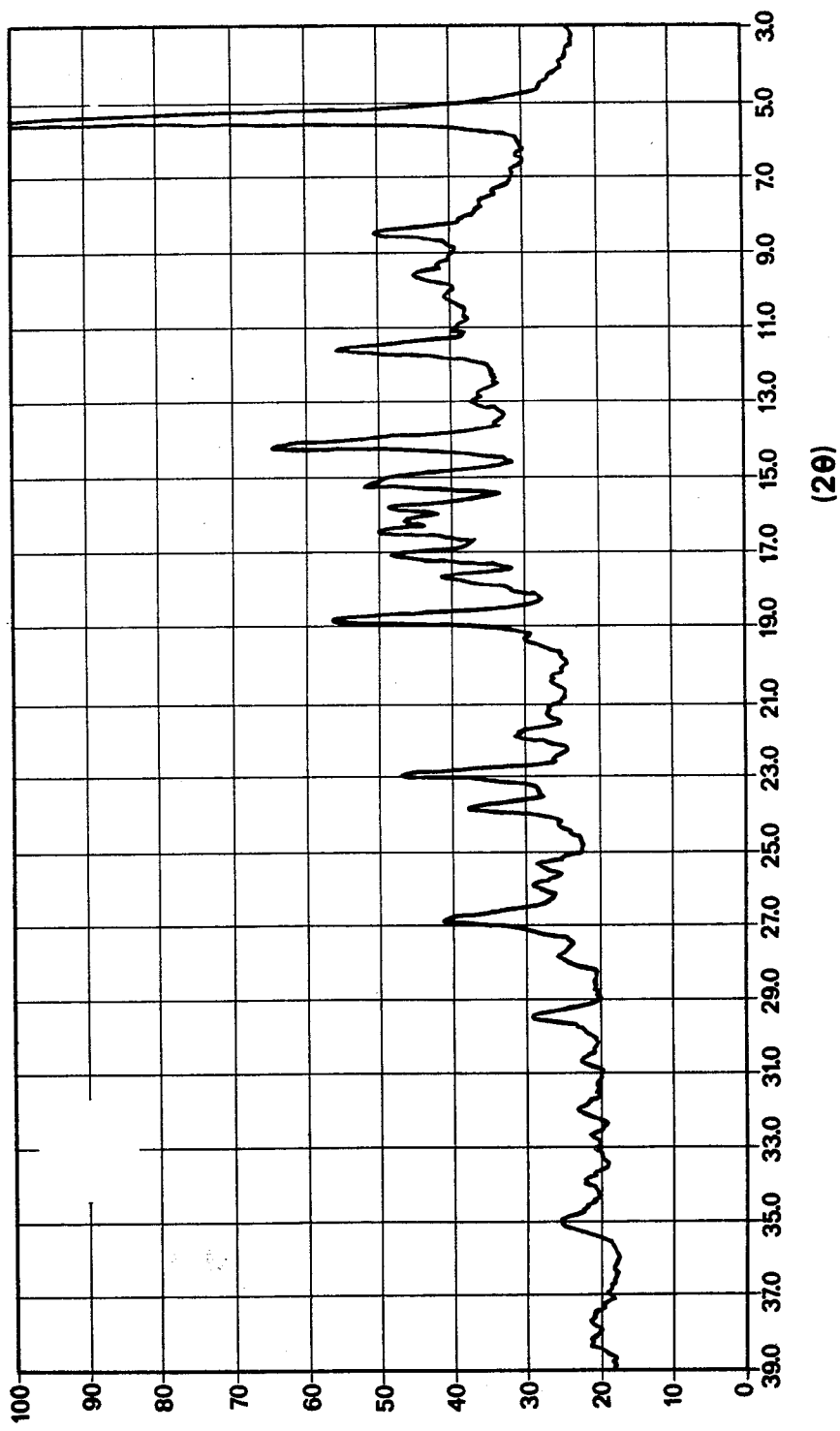

The crystalline pivampicillin is characterized by its IR-spectrum (FIG. 1) and its X-ray Diffraction Pattern (FIG. 2).

In particular it is characterized by having absorption bands in its IR-spectrum at 3360, 3310, 1765–1745, and 1680 $cm^{-1}$, and by having a melting point of 115°–117°C.

Also it is characterized by its solubilities in various solvents of Table I.

Table I

| Solvent | Solubilities at room temperature (about 25°C); mg pivampicillin per ml solution |
|---|---|
| water | 0.1 |
| methanol | > 500 (destruction) |
| ethanol | 40 |
| isopropanol | 12 |
| isopropylether | 1 |
| acetonitrile | 450 |
| cyclohexane | 0.15 |
| light petroleum (bp. 60–80°C) | 0.02 |
| ether | 10 |

The crystalline pivampicillin has thus an extremely low solubility in water, and therefore it is suitable e.g. for preparing suspensions for use in pediatric practice. In addition the crystalline pivampicillin has a higher density than its salts which makes it suitable also for preparing small size dosage units, e.g. tablets, capsules, etc.

It is another object of the invention to provide methods of producing the crystalline pivampicillin.

In the method of the invention the crystalline pivampicillin is produced from non-crystalline or dissolved pivaloyloxymethyl D(-)-α-aminobenzylpenicillinate by crystallizing it in the presence of organic liquids or water or mixtures of such at a temperature below 50°C.

In an appropriate embodiment of the invention, the non-crystalline pivampicillin or a solution thereof is obtained by neutralizing a salt of pivampicillin with an organic or inorganic base.

In the event an organic base is used in the above embodiment, such base may form part of the above crystallization medium.

For instance the pivampicillin hydrochloride can simply be dissolved or suspended in organic liquids or water or a mixture of such, and be neutralized by addition of an inorganic or organic base under formation of the desired crystalline form.

As liquids may appropriately be used lower aliphatic alcohols, such as methanol, ethanol, propanol, isopropanol, butanol; petroleum ether, and higher boiling distillates; cyclohexane; diethyl ether, diisopropyl ether; ethyl acetate; acetone; dimethyl sulfoxide, dimethylformamide; dioxane; and acetonitrile.

In the neutralization process, most inorganic or organic bases can be used, such as alkali metal hydroxides, alkaline earth metal hydroxides, carbonates or bicarbonates, phosphates, acetates or corresponding salts with weak organic acids. Also may be used ammonia, or ammonium carbonate, or carbamates.

Among suitable organic bases, mention may be made of triethanolamine, triethylamine, dimethyl-benzylamine, diisopropylethylamine, diethylamine, and n-propylamine but also basic ion-exchange resins are usable.

It shall be noted that a simultaneous precipitation may occur of the crystalline pivampicillin and a salt of the base used in the process with the acid contained in the pivampicillin salt. In such event, the desired crystalline pivampicillin is recovered by being filtered off and the undesired salt is removed by washing. On the other hand by using an ion-exchange resin, a solution of a pivampicillin salt is appropriately passed through the ion-exchange resin to remove the acid, whereafter the crystalline pivampicillin is precipitated from the solution.

In still another embodiment a solution of pivaloyloxymethyl D(-)-α-azidobenzylpenicillinate in a suitable solvent is catalytically hydrogenated under formation of pivampicillin which is then recovered from the solution after removal of the catalyst. Thus for instance, the crystalline pivampicillin can be recovered by evaporation or precipitation by adding a suitable second solvent. The pivaloyloxymethyl D(-)-α-azidobenzylpenicillinate is a known compound, the preparation of which is described in our British Pat. No. 1,215,812, but other intermediates in which the amino group of the side chain is either protected or replaced by a group which is easily converted into an amino group may be used in the method. Thus, for instance, crystalline pivampicillin can also be obtained by hydrogenating a compound in which the amino group is protected with for instance benzyloxycarbonyl, a related derivative thereof, or with triphenylmethyl, as is more elaborately described in our British Pat. No. 1,215,812.

In a further embodiment, the non-crystalline pivampicillin, or the solution of the same, is obtained in a reaction in which the acid of the pivampicillin salt used as starting material is removed by one of the known reactions under which acids can be bound, e.g. by addition of hydrogen halides to epoxides under formation of halohydrines.

It is still another object of the invention to provide a pharmaceutical preparation containing crystalline pivampicillin for the treatment of infectious diseases.

As is well known, drugs are preferably employed in their crystalline form, such form e.g. being more stable than the amorphous form. Furthermore, the crystalline form of a drug is commonly a necessity in order to fulfil the official requirement as to purity of drugs.

In the clinic, pivampicillin is therefore presently used in the form of its crystalline hydrochloride, which is readily soluble in water. Other salts such as the p-toluenesulphonate, which is slightly soluble in water, has also been proposed for medical use. Such salts, however, have an unpleasant bitter taste, wherefore they are appropriately administered in the form of capsules or tablets, e.g. with coating, but not in suspensions e.g. for pediatric use, as it is extremely difficult to mask the bitter taste in pharmaceutical preparations.

It has now been found that the crystalline pivampicillin advantageously is used in medical preparations being without a bitter taste, and surprisingly still being a stable compound with excellent absorption.

Thus the preparation, the formulation of which is described in Example 20 of the present Specification, had according to chemical analyses a stability corresponding to a decrease in activity in the order of 5% over a 2 years period when stored at 20°C and a relative humidity of 40%. Also it was surprising that the preparation when mixed up with water could be stored in a refrigerator for 2 weeks with a satisfactory stability.

It is specifically an object of the present invention to provide an pharmaceutical preparation for use in the treatment of infectious diseases, which gives rise to a comparatively high level of ampicillin in the blood and various organs after oral administration, which preparation contains the crystalline pivampicillin alone or in combination with other active ingredients mixed up with a solid carrier and/or auxiliary agents.

The above preparation was given to five healthy volunteers (adults), and as will appear from Table II below, gave rise to high serum concentrations and a high urinary recovery, as expressed below in terms of serum concentrations and urinary excretion, respectively.

Table II

SERUM CONCENTRATIONS (mcg per ml) AND URINARY EXCRETION (in per cent of dose administered) OF AMPICILLIN IN FIVE HEALTHY VOLUNTEERS (ADULTS) FOLLOWING ORAL ADMINISTRATION OF 10 ml OF "PIVAMPICILLIN ORAL SUSPENSION" CONTAINING PIVAMPICILLIN BASE CORRESPONDING TO 250 mg AMPICILLIN

| Subject | Hours after administration | | | | | | | | | |
|---|---|---|---|---|---|---|---|---|---|---|
| | Serum concentrations | | | | | | | Urinary excretion | | |
| | ¼ | ½ | 1 | 2 | 3 | 4 | 6 | 0–6 | 6–24 | 0–24 |
| HM | 1.3 | 2.8 | 5.9 | 4.1 | 2.5 | 0.96 | 0.30 | 80 | 3.4 | 83 |
| KA | 1.7 | 4.1 | 7.7 | 3.9 | 1.6 | 1.1 | 0.27 | 68 | 2.4 | 70 |
| BN | 3.6 | 5.3 | 6.4 | 2.5 | 1.1 | 0.45 | 0.14 | 82 | 1.7 | 84 |
| LA | 2.8 | 6.4 | 9.6 | 2.8 | 1.2 | 0.69 | 0.21 | 75 | 1.9 | 77 |
| LPe | 5.4 | 5.8 | 7.7 | 3.3 | 2.1 | 0.81 | 0.23 | 91 | 2.7 | 94 |
| Mean: | 3.0 | 4.9 | 7.5 | 3.3 | 1.7 | 0.80 | 0.23 | 79 | 2.4 | 82 |

In the said preparation, the proportion of therapeutically active material to carrier substance and auxiliary agent can vary between 1% and 95% of the preparation by weight. The preparation in question can either be worked up to pharmaceutical forms of presentation such as tablets, pills or dragees, or the preparation can be filled in medical containers such as capsules. Pharmaceutical organic or inorganic, solid or liquid carriers suitable for enteral administration can be used to make up the preparation. Gelatine, lactose, starch, magnesium stearate, talc, vegetable and animal fats, gum, polyalkylene glycol, or other known carriers for medicaments are all suitable as carriers.

Furthermore, as mentioned above, the preparation may contain other pharmaceutically active components which can appropriately be administered together with the crystalline pivampicillin in the treatment of infectious diseases, such as other suitable antibiotics, among which mention shall in particular be made of pivaloyloxymethyl 6-[(hexahydro-1H-azepin-1-yl)-methyleneamino]-penicillanate and other 6-amidinopenicillanic acid derivatives, which are described in our British Pat. No. 1,293,590.

Such amidinopenicillanic acid derivatives possess strong, antibacterial effect, especially on gram-negative bacteria, and are useful in the form of the free acids and their atoxic salts, but are in preparations according to the present invention in particular useful in the form of their acyloxymethyl esters.

In the preparations above the ratio of the amidinopenicillanic acid derivative to the crystalline pivampicillin is within the range from 5 to 95 per cent.

The pharmaceutical preparation of the present invention is mainly intended for oral use and especially, in the form of a suspension, intended for use in the pediatric practice, but this shall not be considered as being limiting for the present invention.

The chemical substance pivampicillin may under certain conditions be apt to polymerize, or in other ways may change structure, and it is very surprising that the crystalline pivampicillin has now proved to be an excellent and improved ingredient for pharmaceutical preparations.

The invention will now be illustrated by the following non-limiting examples from which the details of the embodiments will be apparent.

EXAMPLE 1

To a stirred mixture of water (50 ml), a saturated aqueous sodium bicarbonate solution (10 ml) and diethyl ether (3.5 ml) at room temperature was gradually added a solution of pivaloyloxymethyl D(-)-α-aminobenzylpenicillinate, hydrochloride (5.0 g) in a mixture of water (75 ml) and ether (5.2 ml). The crystalline precipitate was filtered off and washed with water and diethyl ether to furnish pivampicillin. Its infra-red spectrum appears from FIG. 1 attached hereto.

EXAMPLE 2

Pivampicillin was prepared in the crystalline state by a balanced addition of aqueous solutions of pivampicillin hydrochloride (solution A) and sodium bicarbonate (solution B) to a stirred 7% aqueous diethyl ether solution (500 ml) at 25° C. keeping the pH in the 6.0 – 6.5 range.

Solution A

Pivampicillin hydrochloride (100 g) in water (200 ml), containing diethyl ether (14 ml).

Solution B

Sodium bicarbonate (20 g) in water (200 ml), containing diethyl ether (14 ml).

After completed addition the mixture was allowed to stir for an additional ½ hour. The crystalline product was collected on a filter and washed with water (600 ml) and diethyl ether (200 ml). After air-drying the melting point was 115°–116.5° C.

EXAMPLE 3

To a vigorously stirred solution of pivampicillin hydrochloride (10 g) in water (50 ml) and diethyl ether (3.5 ml) was added a solution of sodium bicarbonate (2 g) in water (20 ml). The addition was complete after 20–30 min. and the mixture was allowed to stir for further 30 min. The crystalline product was filtered off, washed with water (60 ml) and diethyl ether (20 ml), and air-dried to yield pivampicillin with a melting point 114°–116° C.

EXAMPLE 4

To a vigorously stirred solution of sodium bicarbonate (200 g) in distilled water (8 l) and acetonitrile (1.4 l) was added crystalline seed of previously prepared pivampicillin (20 g). Pivampicillin hydrochloride (1 kg) dissolved in water (4 l) was introduced over a period of about 1 hour at room temperture. The rate of addition was reduced during the first 15 minutes.

The mixture was filtered and the residue washed with an isopropanol-water solution (1:4) (5 l), then with isopropanol (2.5 l), and finally with hexane (2.5 l, technical grade, boiling range: 50°–70° C). The crystalline pivampicillin thus obtained was air-dried at room temperature over night.

$[\alpha]_D^{20}$: 216.7°

Purity: 102.4% (iodometric determination, standard: pivampicillin hydrochloride).

In this and the following Examples, the specific rotation was determined by dissolving pivampicillin (100.0 mg) in ethanol (5.0 ml, 99%) in a 10 ml volumetric flask. When dissolved, the flask was filled to the mark with 1/10 N hydrochloric acid.

Similar results were obtained by following the procedure above and substituting acetonitrile by acetone, ethyl acetate, dimethylformamide, or dimethyl sulfoxide.

EXAMPLE 5

To a vigorously stirred solution of sodium bicarbonate (200 g) in water (8 l) and isopropanol (2 l) was added crystalline pivampicillin seed (20 g). Pivampicillin hydrochloride (1 kg) dissolved in water (4 l) and isopropanol (1 l) was introduced over a period of about 1 hour at room temperture. The rate of addition was reduced during the first 15 minutes.

The mixture was filtered and washed with an isopropanol-water solution (1:4, 5 l) then with isopropanol (2.5 l), and finally with hexane (2.5 l, boiling range 50°–70°C). The crystalline pivampicillin thus obtained was air-dried at room temperature over night.

$[\alpha]_D^{20}$: 215.7°

Purity: 100.4% (iodometric determination, standard: pivampicillin hydrochloride).

High yields of crystalline pivampicillin were also obtained by replacing the isopropanol used above by n-butanol, n-propanol, ethanol and methanol.

EXAMPLE 6

To a vigorously stirred mixture of water (50 ml), diisopropyl ether (50 ml), sodium bicarbonate (2 g) and urea (10 g) was added a solution of pivampicillin hydrochloride (10 g) in water (40 ml). The addition was complete after 20–30 min., and the mixture was allowed to stir for further 30 min. The crystalline pivampillin was filtered off and washed with water (60 ml) and diisopropyl ether (20 ml).

EXAMPLE 7

Pivampicillin hydrochloride (25 g) was suspended in cyclohexane (250 ml). Ammonium carbamate (4.0 g) and crystalline seed (0.25 g) were added. After vigorous stirring for 1½ hour, water (125 ml) was added, and the mixture was filtered and the residue washed with water (150 ml) and cyclohexane (150 ml). The crystalline pivampicillin thus obtained was air-dried.

$[\alpha]_D^{20}$: +212°

Similar results were obtained by replacing cyclohexane/ammonium carbamate as used above by diisopropyl ether/ammonium carbonate, hexane/ammonia, and diisopropyl ether/ammonia, respectively.

EXAMPLE 8

Pivampicillin hydrochloride (750 g) was suspended in hexane (6750 ml, technical grade, bp 60°–80° C) containing isopropanol (750 ml). To the well-stirred suspension, triethanol amine (247 g) mixed with isopropanol (375 ml) was added over ca. 60 min. Additional isopropanol (75 ml) was used to rinse the lines.

Stirring was continued for 30 min. then water (3750 ml) was introduced (pH of the water phase ~7). After 30 min. the mixture was filtered and the filter cake was washed with water (7500 ml), isopropanol (1500 ml, −10° C) and hexane (4000 ml, bp. 60°–80°C). The crystalline pivampicillin thus obtained was dried at room temperature.

$[\alpha]_D^{20}$: 215°

Purity: 99.0% (iodometric determination, standard: pivampicillin hydrochloride).

In the above procedure, good results were also obtained when substituting hexane by diisopropyl ether, and replacing triethanolamine by diethanolamine, triethylamine, diethylamine, or n-propylamine, respectively.

EXAMPLE 9

Pivampicillin hydrochloride (10 g) was dispersed in isopropanol (50 ml). Diisopropylethylamine (3.4 ml) was added dropwise while stirring at room temperature, resulting in a clear solution. After 2 hours at 0°C the crystalline pivampicillin was collected on a filter and washed with a little isopropanol and diisopropyl ether.

$[\alpha]_D^{20}$: + 217.2°

Purity: 99.1% (iodometric determination, standard: pivampicillin hydrochloride).

EXAMPLE 10

To a vigorously stirred mixture of distilled water (1 l) containing sodium bicarbonate (40 g) and diisopropyl ether (1 l), crystalline pivampicillin seed (4 g) was added. Pivampicillin hydrochloride (200 g) in water (800 ml) was introduced over 30 min. at room temperature. After stirring for additional 15 min., the slurry was filtered and the residue washed with water (1250 ml) and diisopropyl ether (800 ml). Efficient air-drying for 24 hours left crystalline pivampicillin.

$[\alpha]_D^{20}$: + 215.8°

Purity: 99.3% (iodometric determination, standard: pivampicillin hydrochloride).

By following the procedure above and replacing sodium bicarbonate by disodium hydrogen phosphate, similar results were obtained.

EXAMPLE 11

To a vigorously stirred mixture of pivampicillin hydrochloride (200 g) in water (2 l), and diisopropyl ether (1 l) was added crystalline pivampicillin seed (4 g).

Triethanolamine (59.7 g) in water (300 ml) was introduced over a 30 min. period at room temperature (End point pH: 6.7–6.9). Stirring was maintained for 15 min. and the mixture was filtered. Thorough washing was then performed with water (1.25 l) and finally with diisopropyl ether (600 ml) yielding crystalline pivampicillin with a melting point of 113°–115° C.

$[\alpha]_D^{20}$: + 216°

EXAMPLE 12

To an efficiently stirred mixture of water (250 ml) containing sodium bicarbonate (10 g) and hexane (250 ml, boiling range 60°–80° C), n-butanol (15 ml) and crystalline seed (1 g) were added. Pivampicillin hydrochloride (50 g) dissolved in water (200 ml) was introduced over 1 hour at room temperature. The mixture was filtered and the residue washed with isopropanol-water (1:4) (250 ml), isopropanol (150 ml) and hexane (300 ml, bp. 60°–80° C). Air-drying at 25° C overnight yielded crystalline pivampicillin with a melting point of 114° C.

$[\alpha]_D^{20}$: + 219.1°

EXAMPLE 13

Pivampicillin hydrochloride (12.7 g) was dissolved in water (250 ml) at 0° C. Diethyl ether (500 ml) and sodium bicarbonate (10 g) were added by vigorous stirring. The layers were separated and the ethereal phase was extracted with ice water (250 ml). After drying over magnesium sulphate, the ether solution was partially evaporated in vacuo, causing crystalline, colourless precipitation of the desired compound which was collected on a filter, washed with cold diethyl ether and dried.

Mp.: 113°–115°C;

$[\alpha]_D^{20}$: + 223.8° (c = 1 in 0.1 N HCl).

(I.R. (KBr)) (0.5%): 3360, 3310, 1765–1745, 1680 cm.$^{-1}$

| Elementary analysis: | C | H | N | S |
|---|---|---|---|---|
| Calculated for $C_{22}H_{29}N_3O_6S$: | 57.00 | 6.30 | 9.07 | 6.92% |
| Found: | 56.97 | 6.34 | 8.90 | 7.05% |

EXAMPLE 14

Pivampicillin tosylate, hydrate (13.1 g) was stirred with isopropanol (50 ml) at 0°C, while diisopropylethylamine (3.45 ml) was added dropwise. After 30 min. the crystalline precipitate was collected by filtration, washed with isopropanol (25 ml) and hexane (50 ml, bp. 60°–80°), and air-dried, yielding crystalline pivampicillin with a melting point of 114°–116°C.

EXAMPLE 15

Pivampicillin tosylate, hydrate (13.1 g) was suspended in t-butanol (50 ml). While stirring at 25°C., triethylamine (2.75 ml) was added. The resulting clear solution was stirred for 1 hour, while precipitating. The crystalline pivampicillin was collected by filtration, washed with t-butanol (25 ml) and hexane (bp 60°–80°C) (50 ml), and air-dried.

EXAMPLE 16

Pivampicillin hydrochloride (10 g) was added to propylene oxide (40 ml) at 0°C and the solution was left for 20 hours at 0°C. Propylene oxide was drawn off in vacuo and the residue was stirred with isopropanol (40 ml). The crystalline product was filtered off, washed with isopropanol (25 ml) and hexane (50 ml, b.p. 50°–70°C) and finally air dried.

EXAMPLE 17

A solution of pivaloyloxymethyl D(-)-α-azidobenzylpenicillinate (9.8 g) in a mixture of ethyl acetate (50 ml) and isopropanol (200 ml) was flushed with nitrogen.

10% palladium-on-charcoal catalyst (5 g) was added, and hydrogen was passed through the mixture, while stirring at 0°C for 1 hour. The catalyst was filtered off, and ethyl acetate was removed from the filtrate by partial evaporation in vacuo. Isopropanol was added (100 ml), and the volume was finally reduced to 50 ml, causing gradual crystallization of pivampicillin, which was collected by filtration, washed with isopropanol, and air-dried. Melting point: 113°–116° C.

$[\alpha]_D^{20}$: +213.3°

EXAMPLE 18

Preparation of tablets each containing 0.324 g of pivampicillin.

| Ingredients: | Gram |
|---|---|
| Pivampicillin | 324 |
| Lactose | 91 |
| Polyvinylpyrrolidone | 7 |
| Corn Starch | 50 |
| Talc | 25 |

-continued

| Ingredients: | Gram |
|---|---|
| Magnesium stearate | 3 |

The pivampicillin and the lactose are screened through a 20 mesh per linear inch sieve and mixed together for 15 minutes. Thereafter the mixed powders are wetted with an aqueous solution of polyvinylpyrrolidone. The moist mass is passed through a 10 mesh per linear inch screen and then dried at 38° centigrade. When the water has evaporated, the granules are broken on a 16 mesh per linear inch sieve and mixed with the corn starch, talc and magnesium stearate. The granulate is compressed into tablets of 0.50 gram weight using 16/32 inch punches and dies, yielding 1000 tablets each containing 0.324 g of pivampicillin.

EXAMPLE 19

Capsules are prepared in accordance with the following description.

| Ingredients: | Gram |
|---|---|
| Pivampicillin | 324 |
| Magnesium stearate | 3 |
| Talc | 17 |

The ingredients are passed through a 60 mesh per linear inch sieve and mixed for 15 minutes. The mixture is filled into No. 0 gelatine capsules (Parke, Davis & Co.) using a semi-automatic capsule-filling machine shaken by vibrator. Each capsule contains 344 mg and the mixture corresponds to 324 mg of pivampicillin.

EXAMPLE 20

Oral suspension for use in pediatric practice. The mixture consists, per dose, of the following ingredients:

| Pivampicillin | 162 mg |
|---|---|
| Carboxymethylcellulose | 15 mg |
| Sorbitol, finely crystalline | 2000 mg |
| Flavour additives etc | 50 mg |
| Auxiliary agents | 50 mg |

The pivampicillin is mixed with half of the sorbitol. The mixture is screened through a 50 US standard mesh sieve. The other components are individually screened through a 50 US standard mesh sieve and thereafter mixed together with the pivampicillin above. The compounds are thoroughly mixed and finally screened through a 40 US standard mesh sieve. Addition of 3.3 ml of water gives 5 ml of suspension after shaking for ½ - 1 minute.

The formulation above was used in a clinical trial and given to children of the age 1 - 3 years (6 patients) hereafter called group A, and to infants of the age 0 - 1 years (10 patients) hereinafter called group B.

The table III below illustrates the average serum concentration of ampicillin following the oral administration of 162 mg pivampicillin (~125 mg ampicillin) in the form of the suspension above to each individual of the group A and doses containing 81 mg pivampicillin (~62,5 mg ampicillin) to each individual of the group B:

Table III

| Group A 1 - 3 years | | Group B 0 - 1 years | |
|---|---|---|---|
| Hours after Administration | Serum Conc. mcg/ml | Hours after Administration | Serum Conc. mcg/ml |
| 0.25 | 2.84 | 0.25 | 1.50 |
| 0.50 | 5.13 | 0.50 | 2.66 |
| 0.75 | 5.53 | 0.75 | 3.41 |
| 1.0 | 5.94 | 1.0 | 3.56 |
| 2.0 | 4.67 | 2.0 | 1.97 |
| 3.0 | 2.87 | 3.0 | 1.17 |
| 4.0 | 1.19 | 4.0 | 0.55 |
| 6.0 | 0.25 | 6.0 | 0.10 |

The above administration of 162 mg and 81 mg pivampicillin, respectively, corresponds in average in group A to 14.4 mg/kg pivampicillin and in group B to 12.7 mg/kg pivampicillin.

As will appear from the figures above a rapid and excellent absorption is obtained.

EXAMPLE 21

Capsules, each containing 0.138 g of pivaloyloxymethyl 6-[(hexahydro-1H-azepin-1-yl)-methyleneamino]-penicillanate and 0.162 g of pivampicillin are prepared according to the following procedure:

| Ingredients: | |
|---|---|
| Pivaloyloxymethyl 6-[(hexahydro-1H-azepin 1-1yl)-methyleneamino]-penicillanate | 138 g |
| Pivampicillin | 162 g |
| Polyvinylpyrrolidone | 10 g |
| Magnesium stearate | 4 g |

The pivaloyloxymethyl 6-[(hexahydro-1H-azepin-1-yl)methyleneamino]-penicillanate and the pivampicillin are mixed and passed through a 20 US Standard mesh sieve. After having been mixed again, the resulting powder is moistened with a solution of polyvinylpyrrolidone in water (150 ml). The moistened mixture is granulated by passing it through a 20 US Standard mesh sieve and is afterwards dried by 30°C. For the drying operation, a conventional drying oven with trays, or other suitable drying apparatus, for instance functioning according to the fluidized bed principle, may be applied.

After drying, the granulate is passed through a 25 US Standard mesh sieve and is finally mixed with the magnesium stearate.

The finished granulate is filled into hard gelatine capsules No. 0, each capsule containing about 0.325 g granulate the above ingredients thereby corresponding to 1000 capsules.

EXAMPLE 22

Tablets, each containing 0.138 g of pivaloyloxymethyl 6-[(hexahydro-1H-azepin-1-yl)-methyleneamino]-penicillanate and 0.162 g of pivampicillin are prepared according to the following procedure:

| Ingredients: | |
|---|---|
| Pivaloyloxymethyl 6-[-(hexahydro-1H-azepin--1-yl)-methyleneamino]-penicillanate | 138 g |
| Pivampicillin | 162 g |
| Polyvinylpyrrolidone | 10 g |
| Cellulose, microcrystalline | 175 g |
| Starch | 100 g |
| Magnesium stearate | 4 g |

The pivaloyloxymethyl 6-[(hexahydro-1H-azepin-1-yl)-methyleneamino]-penicillanate and the pivampicillin are mixed and passed through a 20 US Standard mesh sieve. After having been mixed again, the resulting powder is moistened with a solution of polyvinylpyrrolidone in water (150 ml). The moistened mixture is granulated by passing it through a 20 US Standard mesh sieve and is afterwards dried by 30°C. For the drying operation, a conventional drying oven with trays or other suitable drying apparatus, for instance functioning according to the fluidized bed principle, may be applied.

After drying, the granulate is passed through a 25 US Standard mesh sieve and is afterwards mixed with the microcrystalline cellulose, the starch and the magnesium stearate. The granulate is compressed into tablets, each containing about 0.600 g, by using punches with a diameter of 13.5 mm, the above ingredients thereby corresponding to 1000 tablets.

EXAMPLE 23

For peroral administration especially useful in the pediatric therapy the following mixture, intended for suspension in water or another drinkable liquid immediately before use, is produced. The mixture consists, per dosage, of the following ingredients:

| | |
|---|---|
| Pivaloyloxymethyl 6-[(hexahydro-1H-azepin--1-yl)-methyleneamino]-penicillanate | 138 mg |
| Pivampicillin | 162 mg |
| Methylcellulose | 10 mg |
| Sugar | 2.2 g |
| Saccharin sodium | 8 mg |
| Flavour additives | 9.5. |

This dosage is intended for being suspended in about 5 ml of a suitable liquid.

What we claim is:

1. Crystalline pivaloyloxymethyl D(-)-α-aminobenzylpenicillinate of the formula:

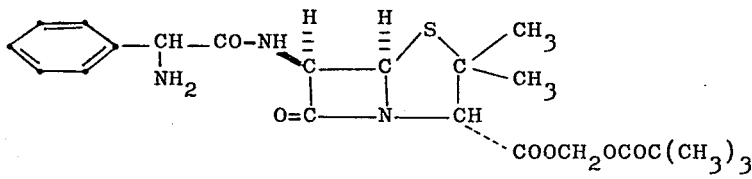

and having the following characterizing data: Infra-red spectrum (KBr, 0,5%) having strong absorption bands at: 3360, 3310, 1765–1745, 1680 cm$^{-1}$ as will appear from FIG. 1 attached hereto and a melting point of 115°–117°C.

* * * * *

UNITED STATES PATENT OFFICE
CERTIFICATE OF CORRECTION

Patent No. 3,956,279      Dated May 11, 1976

Inventor(s) Ernst Torndal Binderup, Hans Jorgen Petersen and Sven Liisberg

It is certified that error appears in the above-identified patent and that said Letters Patent are hereby corrected as shown below:

On the title page of the patent the following should be added:

--[30] Foreign Application Priority Data
    October 6, 1972    United Kingdom      46317/72 --.

Signed and Sealed this

Twentieth Day of July 1976

[SEAL]

Attest:

RUTH C. MASON
*Attesting Officer*

C. MARSHALL DANN
*Commissioner of Patents and Trademarks*